United States Patent [19]
Avrahami

[11] Patent Number: 5,983,135
[45] Date of Patent: Nov. 9, 1999

[54] TRANSDERMAL DELIVERY OF FINE POWDERS

[76] Inventor: Zohar Avrahami, 40 Binyamin Street, Rehovot 76241, Israel

[21] Appl. No.: 09/220,712

[22] Filed: Dec. 24, 1998

[51] Int. Cl.[6] .................................................. A61N 1/30
[52] U.S. Cl. ............................................ 604/20; 607/115
[58] Field of Search ................................ 604/20, 21, 67; 607/149–152, 115

[56] References Cited

PUBLICATIONS

Microdose Technology, Inc., Company Business Overview, Sep. 98, USA.
Delsys Pharmaceutical Corp., of Princeton, New Jersey.

*Primary Examiner*—Wynn Wood Coggins
*Assistant Examiner*—Sharon Finkel
*Attorney, Agent, or Firm*—Abelman, Frayne & Schwab

[57] ABSTRACT

A device for delivery of a powder to the skin of a subject includes a pad, made of an insulating material and having an upper side and a lower side, which lower side is placed against the skin after application of the powder thereto. An electrical power source applies an electrical potential to the pad, causing the powder to adhere by electrostatic force to the lower side of the pad, and then alters the potential so that the powder is released from the pad and contacts the skin against which the pad is placed.

33 Claims, 5 Drawing Sheets

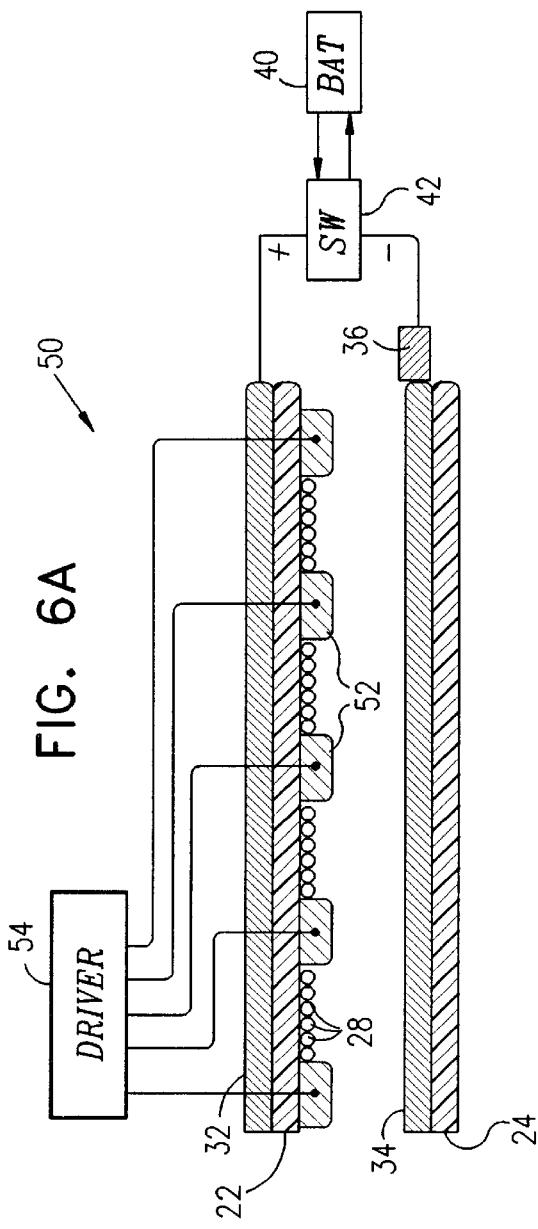
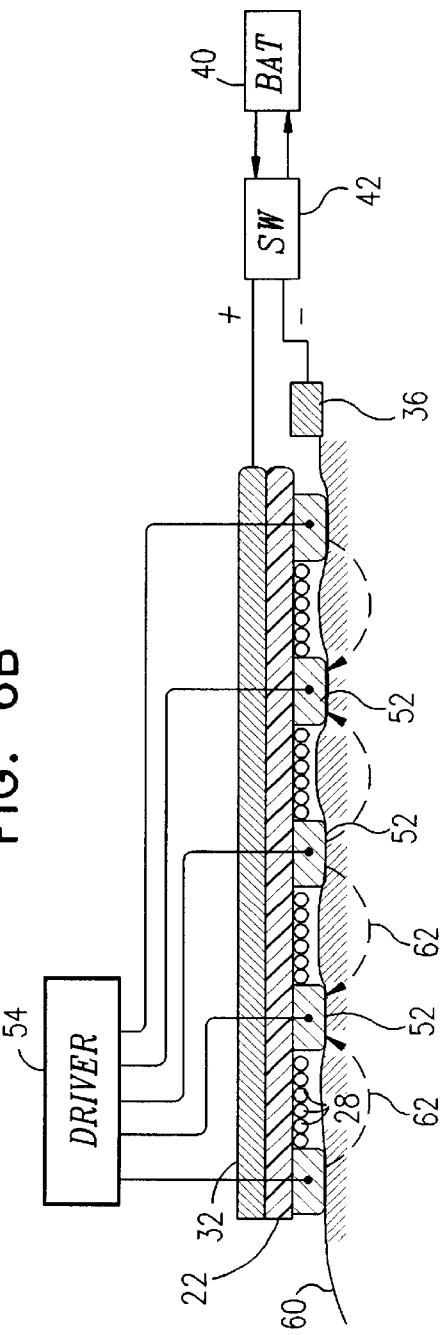

TRANSDERMAL DELIVERY OF FINE POWDERS

FIELD OF THE INVENTION

The present invention relates generally to drug delivery devices and methods, and specifically to transdermal drug delivery patches.

BACKGROUND OF THE INVENTION

Ultra-fine, dry powders, also known as micro- and nano-powders, are the subject of increasing interest in pharmaceutical manufacturing, because they provide a solution to many of the shortcomings of blended drugs. Active drug ingredients are produced, packaged and administered to the patient as pure, dry powders, without blending them with solvents or other agents. Elimination of the blending steps simplifies the manufacturing process, reduces development and manufacturing costs, makes dosage more accurate, and extends the drug's shelf life.

The drawback of dry powders is that they are difficult to handle, tending to clump and stick in storage and to scatter when disturbed by even slight air movements. These handling problems must be overcome if dry powder drugs are to be used efficiently and safely, and special methods must be used for accurate dose processing and administration. A number of companies, such as Delsys Pharmaceutical Corp., of Princeton, N.J., have developed pharmaceutical manufacturing processes using electrostatic forces to deposit fine powders onto a substrate. Electrostatic deposition is the same principle as is used in dry-toner copying machines. The technique is used to form and encapsulate dry powders into pills for oral administration.

Other drug delivery modalities have been adapted for use with dry powders. For example, dry powder inhalers have gained acceptance in drug delivery to the lungs. PowderJect Pharmaceuticals plc, of Oxford, England, is developing a powder injection device for intradermal delivery of vaccines and other drugs. The device shoots powder particles into the skin at supersonic speed, taking the place of a syringe.

SUMMARY OF THE INVENTION

It is an object of the present invention to provide devices and methods for transdermal delivery of dry powders.

In preferred embodiments of the present invention, a powder delivery patch comprises an electrostatic pad and an electrical power source. In preparation for application of a dry powder, such as a drug in powder form, to the skin of a subject, the power source applies an electrical potential to the pad, which causes the powder to adhere by electrostatic force to a lower side of the pad. This side is placed against the skin, and the electrical potential on the pad is reversed. The resultant electrostatic force drives the powder off the pad and onto the skin, through which the powder is absorbed into the body.

In some preferred embodiments of the present invention, the powder delivery patch is produced in the form of a disposable plastic envelope, including upper and lower surfaces. The electrostatic pad preferably serves as the upper surface, and the lower surface is removable, as described hereinbelow. Electrically-conductive coatings, preferably metallized coatings, are formed on the outside of the upper surface (i.e., the upper side of the pad) and on the inside of the lower surface. The envelope is filled with a desired dose of dry powder. In the absence of any electric field between the two surfaces, however, the powder particles clump and stick together at random inside the envelope.

Preferably, the power source is contained in an electronic control unit, which is coupled to the pad. The control unit applies a voltage between the upper and lower conductive coatings, so that the inside of the upper surface of the envelope becomes charged with static electricity of a first polarity (which may be positive or negative). Preferably, the powder particles comprise insulating material and carry a charge of a second, opposite polarity. Alternatively, if the powder particles are wholly or partially conductive, the conductive coating inside the lower surface passes charges of the opposite polarity to the powder particles. In either case, the particles are consequently attracted to the upper surface. The charges cause the particles to repel one another, so that they adhere to the inside of the upper surface in a uniform layer. Preferably, although not necessarily, the polarity is first varied several times to completely de-aggregate the powder, after which the polarity is held fixed.

With the powder adhering to the upper surface, the lower surface of the envelope is peeled away, exposing the powder. The upper surface is placed against the skin to release the powder, as described hereinabove. Preferably, the upper surface is held in place against the skin by a layer of adhesive around the edges of the patch.

In some preferred embodiments of the present invention, the dry powder delivered by the patch to the skin passes through the skin by passive absorption. In this mode of operation, skin moisture preferably mobilizes the powder particles so that they migrate through the epidermis.

In other preferred embodiments of the present invention, the patch is used together with suitable methods of skin puncture or ablation in order to enhance skin penetration by the powder. In one such embodiment, the patch comprises an array of electrodes, which are driven to electrically ablate small channels through the stratum corneum (the tough outer layer of the skin). The powder then passes through the skin via these channels. Preferred methods of electrical ablation for this purpose are described in a U.S. patent application 09/189,170, entitled "Transdermal Drug Delivery and Analyte Extraction," filed Nov. 9, 1998, which is assigned to the assignee of the present patent application and incorporated herein by reference.

In some preferred embodiments of the present invention, the dry powder is driven off the pad gradually over a period of time, at a predetermined dosage rate. Preferably, the control unit is programmed to release the powder from the pad one region at a time. Each region provides a timed sub-dose out of the total dosage stored in the envelope.

In some preferred embodiments of the present invention, the control unit is coupled to a sensor on the patch, and controls the power source responsive to signals from the sensor. Preferably, the sensor comprises one or more electrodes, and the control unit detects changes in electrical resistance between the electrodes. The sensor signals enable the control unit to determine when one or more of the following events have taken place: attachment of the control unit to the pad; removal of the lower surface of the envelope; and contact of the pad with the skin.

There is therefore provided, in accordance with a preferred embodiment of the present invention, a device for delivery of a powder to the skin of a subject, including:

a pad, including an insulating material and having an upper side and a lower side, which lower side is placed against the skin after application of the powder thereto; and an electrical power source, which applies an electrical potential to the pad, causing the powder to adhere by electrostatic force to the lower side of the pad, and which alters the potential so that the powder is released from the pad and contacts the skin against which the pad is placed.

Preferably, the pad includes an electrically conductive coating on the upper side thereof, to which the power source applies the potential. In a preferred embodiment, the conductive coating is segmented, such that the power source reverses the polarity of the potential substantially independently in two or more segments of the coating.

Preferably, the device includes an envelope in which the powder is contained before delivery of the powder to the skin, the envelope including an upper and a lower surface, wherein the upper surface includes the pad, and the lower surface is separated from the pad before the lower side of the pad is placed against the skin.

Preferably, the envelope includes an electrically conductive region therein, which contacts the powder in the envelope and imparts electrical charge thereto to the extent that the powder is at least partially electrically conductive. Most preferably, the power source applies the electrical potential between the upper and lower surfaces of the envelope, and wherein the electrically conductive region includes a conductive coating on the lower surface. Further preferably, the device includes a conductor coupled to the power source, which contacts the skin after the lower surface is separated from the pad so that the power source applies the electrical potential between the pad and the skin.

Preferably, the power source includes a battery and a switching circuit coupled thereto, wherein the switching circuit includes a voltage converter, which steps up a voltage supplied by the battery so that the electrical potential applied to the pad is substantially greater than the battery voltage.

Further preferably, the switching circuit includes a polarity switch, which applies the electrical potential to the pad, causing the powder to adhere thereto, at a first polarity, and which reverses the polarity so as to cause the powder to be released.

In a preferred embodiment, the device includes a sensor, which generates a signal responsive to an operational state of the device, wherein the switching circuit receives the signal from the sensor and controls operation of the device responsive thereto. Preferably, the sensor includes an electrode, which senses an electrical resistance that varies responsive to the operational state. Further preferably, the power source is fixed to the pad before operation thereof, and the sensor generates the signal responsive to fixing of the power source to the pad. Alternatively or additionally, the sensor generates the signal responsive to opening of the envelope in preparation for placing the pad against the skin and/or responsive to placement of the pad against the skin.

In another preferred embodiment, the device includes means for ablating an outer layer of the skin through which the powder is delivered, wherein the means for ablating preferably includes an array of electrodes between which an electrical current is driven so as to create channels through the outer skin layer. Preferably, the electrodes in the array are mutually spaced by less than about 0.3 mm, and the electrical current is driven between the electrodes at a frequency greater than about 100 Hz.

There is also provided, in accordance with a preferred embodiment of the present invention, a container for a fine powder, including:

an envelope for containing the powder and including an electrically conductive region therein communicating with the powder; and an electrical power source, coupled to apply an electrical potential to the conductive region, whereby electrical charge is applied to the powder in the envelope to the extent that the powder is at least partially electrically conductive, and the powder is manipulated by varying the potential.

Preferably, the power source includes a polarity switch, which reverses a polarity of the potential so as to de-aggregate the powder. Further preferably, the power source applies the potential between the conductive region and an opposing surface of the envelope, such that the powder adheres to the opposing surface.

There is further provided, in accordance with a preferred embodiment of the present invention, a method for delivery of a powder to the skin of a subject, including:

bringing a quantity of the powder into proximity with a pad having upper and lower sides;

applying an electrical potential to the pad, so that the powder adheres to the lower side of the pad by electrostatic force;

placing the lower side of the pad with the powder against the skin; and altering the electrical potential, so that the powder is released from the pad and contacts the skin against which the pad is placed.

Preferably, bringing the quantity of the powder into proximity with the pad includes filling an envelope with the powder, the envelope including an upper and a lower surface, the upper surface including the pad, and placing the lower side of the pad against the skin includes separating the lower surface from the pad before the lower side of the pad is placed against the skin. Further preferably, applying the electrical potential includes applying a potential to an electrically conductive region in the envelope, which contacts the powder in the envelope and imparts electrical charge thereto.

Preferably, applying the electrical potential includes applying a potential between the upper and lower surfaces of the envelope. Most preferably, applying the electrical potential includes applying potential of a first polarity, and altering the electrical potential includes reversing the polarity, wherein the electrical potential of reversed polarity is preferably applied between the pad and the skin.

In a preferred embodiment, an outer layer of the skin through which the powder is delivered is ablated, wherein ablating the outer layer preferably includes applying an electrical current through the skin so as to create channels through the outer skin layer. Most preferably, applying the electrical current includes applying an alternating current.

In another preferred embodiment, altering the potential includes altering the potential in a graduated manner so that the powder is delivered over time in a sequence of sub-doses. Preferably, the pad includes multiple regions, and altering the potential includes altering the potential at different times in two or more of the regions, so that the powder is delivered from the different regions of the pad at the different, respective times.

In still another preferred embodiment, the method includes sensing an operational state of the pad, and controlling the delivery of the powder responsive to the state. Preferably, sensing the operational state includes detecting placement of the lower side of the pad against the skin, and controlling the delivery includes providing a control signal to alter the electrical potential after the placement is detected. Further preferably, sensing the operational state includes sensing an electrical resistance indicative of the state.

There is moreover provided, in accordance with a preferred embodiment of the present invention, a method for manipulating a fine powder, including:

filling an envelope having an electrically conductive region therein with a quantity of the powder, such that the conductive region communicates with the powder; and applying an electrical potential to the conductive region, whereby electrical charge is applied to the powder in the envelope.

Preferably, applying the potential includes de-aggregating the powder.

Most preferably, the method includes varying the electrical potential applied to the conductive region so as to manipulate the powder in the envelope, wherein varying the potential preferably includes reversing a polarity of the potential.

Further preferably, applying the potential includes applying the potential between the conductive region and an opposing surface of the envelope, so that the powder adheres to the opposing surface.

The present invention will be more fully understood from the following detailed description of the preferred embodiments thereof, taken together with the drawings in which:

BRIEF DESCRIPTION OF THE DRAWINGS

FIGS. 6A, 6B and 6C are schematic, sectional illustrations of a device for ablating channels through an outer layer of the skin and delivering a dry powder into the channels, shown respectively in successive operating modes of the device, in accordance with a preferred embodiment of the present invention.

DETAILED DESCRIPTION OF PREFERRED EMBODIMENTS

Figure 1:
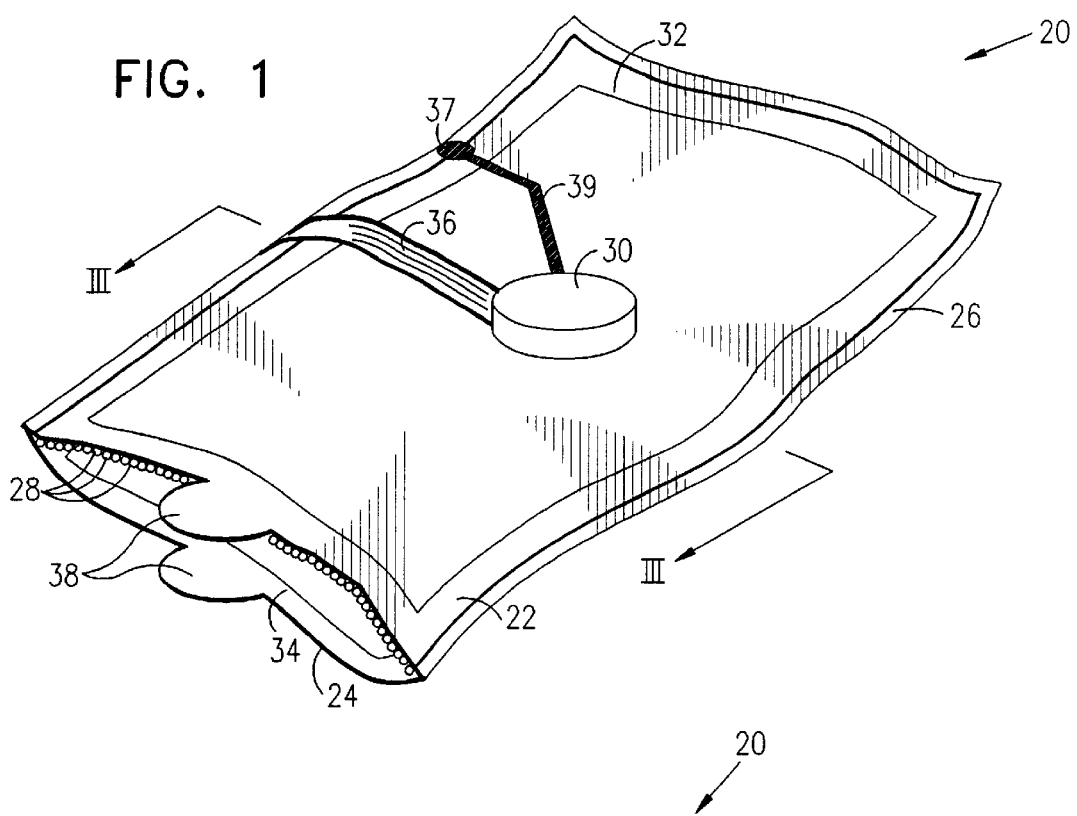
FIG. 1 is a schematic, pictorial illustration of a device for delivery of a dry powder to the skin, in accordance with a preferred embodiment of the present invention.

Reference is now made to FIG. 1, which is a schematic, pictorial illustration of a device 20 for delivery of a fine dry powder 28 to the skin of a subject, in accordance with a preferred embodiment of the present invention. Device 20 has the general form of an envelope, comprising an upper surface 22 and a lower surface 24, joined around a periphery thereof by an adhesive strip 26. The envelope is filled with powder 28, which preferably comprises a drug or other medicinal preparation of any suitable type known in the art, in a quantity corresponding to a predetermined dosage thereof. Although particles of powder 28 are shown in FIG. 1 to be adhering in a generally uniform layer to the inside of upper surface 22, in accordance with a mode of operation of device 20 described hereinbelow, ordinarily the powder tends to aggregate in uneven clumps inside the envelope.

Figure 2A:
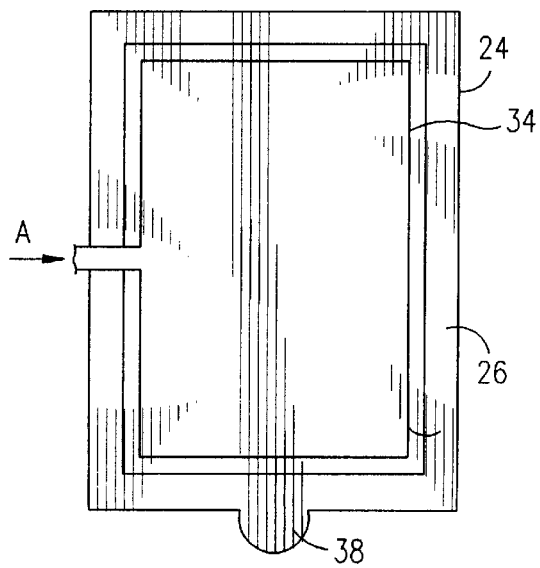
FIGS. 2A and 2B are schematic top views of lower and upper surfaces of the device of FIG. 1.
Figure 2B:
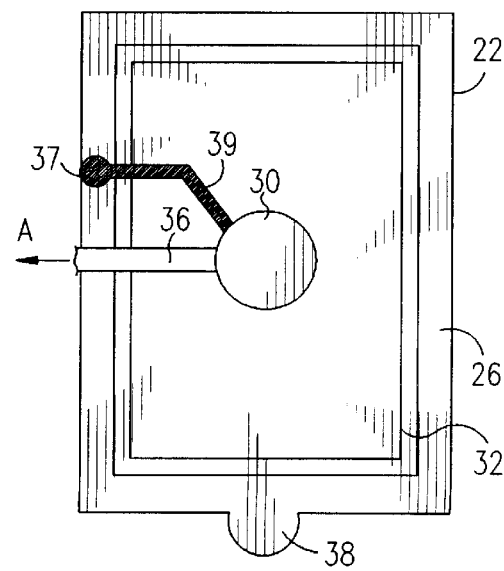
Figure 3:
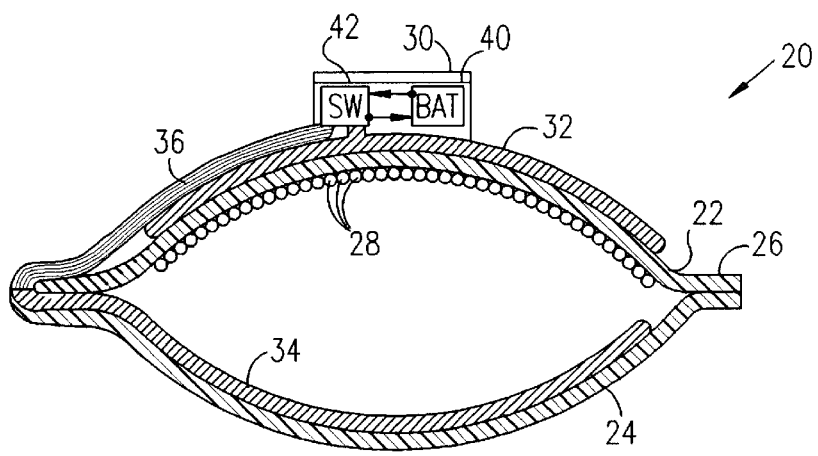
FIG. 3 is a schematic, sectional view of the device of FIG. 1, taken along line III—III.
Figure 5:
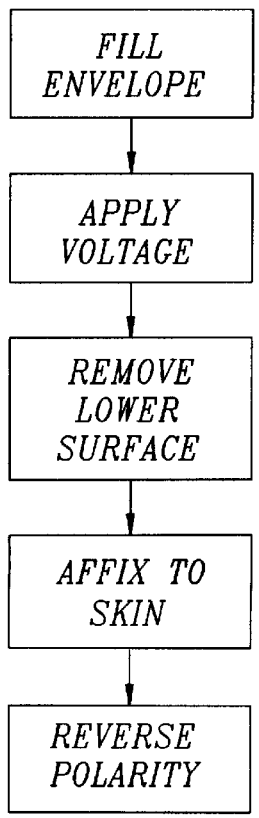
FIG. 5 is a flow chart that schematically illustrates a method for delivering a dry powder to the skin, in accordance with a preferred embodiment of the present invention.
Figure 4:
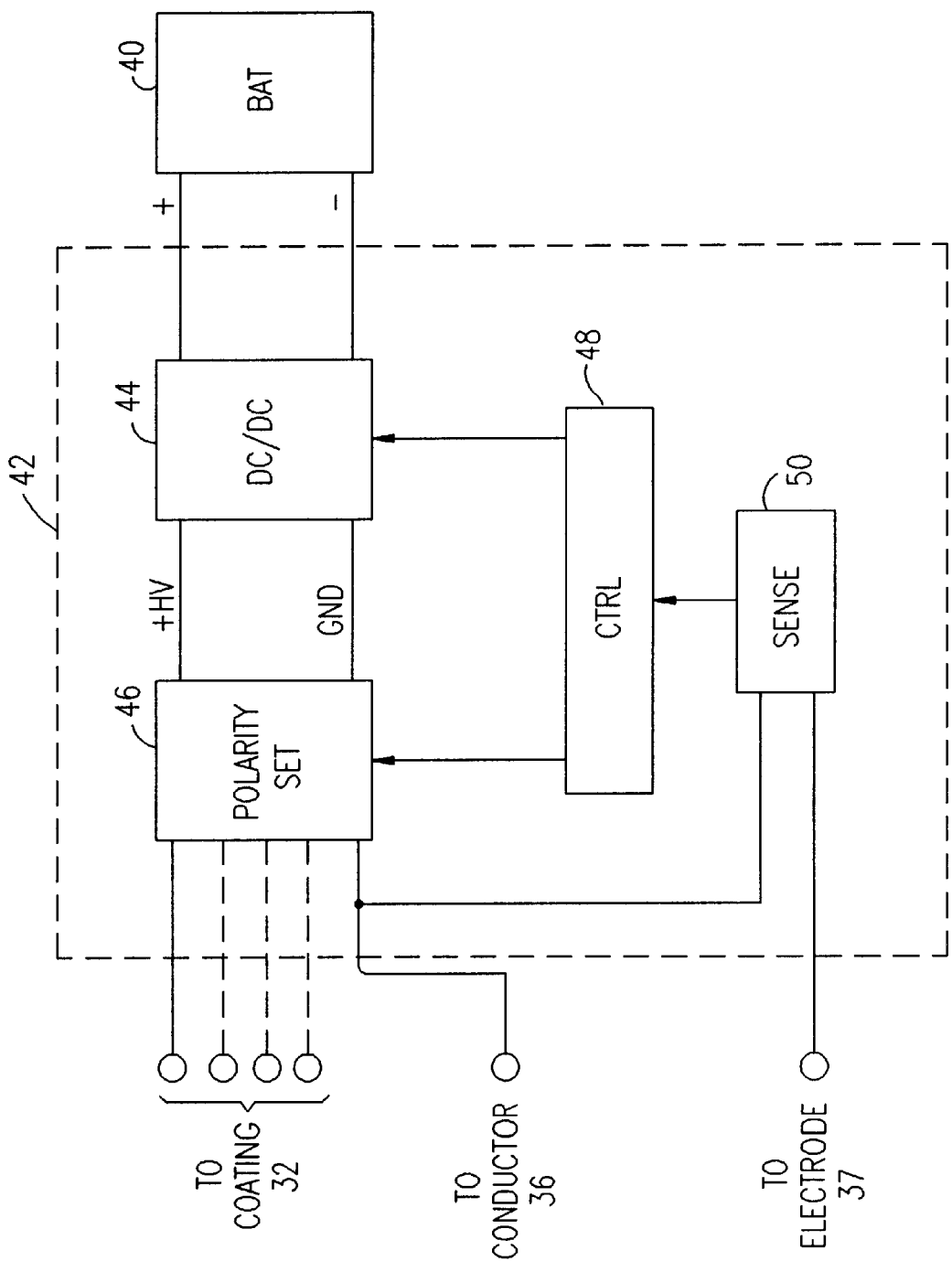
FIG. 4 is a schematic block diagram showing control circuitry for use with the device of FIG. 1, in accordance with a preferred embodiment of the present invention.
Figure 6C:
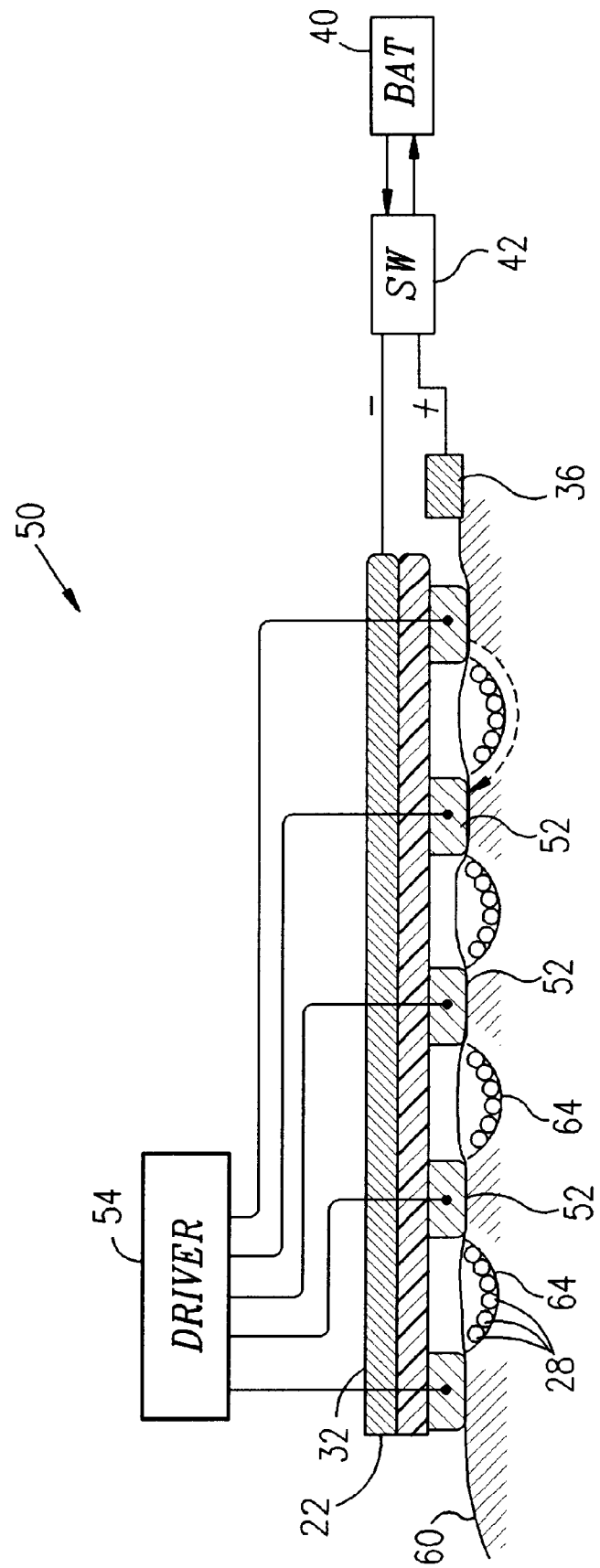

FIGS. 2A, 2B and 3 show different views of device 20, useful in understanding the details of its construction and operation. FIGS. 2A and 2B are top views of lower surface 24 and upper surface 22 respectively. FIG. 3 is a sectional view through device 20, taken along line III—III in FIG. 1. Surfaces 22 and 24 are preferably made of a flexible, non-conducting substance, most preferably a biocompatible plastic, such as a PVC film. Conductive coatings 32 and 34 are deposited respectively on the upper sides of surfaces 22 and 24. Thus, coating 32 is on the outside of the envelope and is insulated from powder 28 by surface 22, while coating 34 is inside the envelope, in contact with the powder. Preferably, the coatings comprise a noble metal that is chemically compatible with the powder, such as gold plating or aluminum.

An electronic control unit 30 comprises a battery 40, and a switching circuit 42. The switching circuit comprises a high-voltage converter (shown in FIG. 4) to step up the voltage supplied by the battery, and applies the stepped-up voltage between coatings 32 and 34. The circuit is coupled to coating 34 by a conductor 36, which is insulated from coating 32. Circuit 42 allows the polarity of the voltage output by unit 30 to be reversed, and may also perform other control functions, as described further hereinbelow. Preferably, with the exception of the control unit, device 20 is a single-use, disposable item, and control unit 30 is capable of snapping on and off a mating connector (not shown) on upper surface 22 after use, for re-use with another powder envelope.

FIG. 4 is a schematic block diagram showing details of control unit 30, in accordance with a preferred embodiment of the present invention. A DC/DC converter 44 steps up the voltage from battery 40 to a high voltage suitable for handling powder 28, preferably in the range of 300 to 10,000 VDC, most preferably about 1,000 VDC. A polarity switch 46 applies the voltage between coatings 32 and conductor 36, varying between positive and negative polarity in the course of use of device 20. Preferably, converter 44 and switch 46 are controlled by a microcontroller 48, comprising a microprocessor and/or dedicated logic circuitry.

Preferably, microcontroller 48 receives signals from a sensing circuit 50 indicative of the status of device 20, and controls the device accordingly, as described hereinbelow with reference to FIG. 5. Most preferably, the sensing circuit measures electrical resistance between conductor 36 and an electrode 37 on the lower side of upper surface 22. Electrode 37 is coupled to circuit 50 by a conductor 39, as shown in FIGS. 1 and 2B. Alternatively or additionally, control unit 30 comprises a user input, such as one or more push-buttons (not shown in the figures), by means of which a user controls the operation of the device. Other modes of user control and of automatic, sensor-based control of device 20 will be apparent to those skilled in the art.

FIG. 5 is a flow chart that schematically illustrates a method for using device 20 to administer powder 28 to the skin, in accordance with a preferred embodiment of the present invention. The envelope is filled with a predetermined quantity of the powder, and is then closed for storage. Preferably, when it is time to use the device, control unit 30 is coupled to upper surface 22, as shown in FIG. 1. Sensing circuit 50 detects a low resistance between conductor 36 and electrode 37, which are electrically coupled by mutual contact with conductive coating 34. Responsive to the low resistance detected by circuit 50, microcontroller 48 initiates automatic operation of the device.

Microcontroller 48 actuates DC/DC converter 44 and polarity switch 46 in order to apply a voltage between coatings 32 and 34. Preferably, switch 46 is operated to alternate the polarity of the voltage for several cycles, typically at a frequency of about 10 Hz, in order to facilitate de-aggregation of the powder. Following de-aggregation, coating 32 is held at a positive voltage relative to coating 34, preferably by about 1000 volts, depending on the properties of powder 28 and the physical design of device 20. Particles of powder 28 preferably comprise insulating material and are negatively charged. Alternatively, to the extent that the particles are wholly or partially conductive, they pick up negative electrical charge from coating 34, with which they are in contact. In either case, the particles are consequently attracted to the inside of surface 22. Because surface 22 is itself non-conductive, and because the negative charges on the powder particles repel one another, the particles tend to de-aggregate and adhere to the inside of surface 22 in a generally uniform layer, as shown in FIGS. 1 and 3.

While powder 28 is held against upper surface 22 by the voltage from circuit 42, a user of device 20 grasps tabs 38 and peels lower surface 24 away from upper surface 22. Removal of the lower surface is detected by sensing circuit 50 as an increase in resistance between conductor 36 and electrode 37. The upper surface is now ready to serve as a pad for transdermal delivery of the powder. Adhesive strip 26, remaining around the periphery of upper surface 22, is used to affix the pad to the skin. Preferably, conductor 36 also contacts the skin, so that the voltage that was previously applied between upper surface 22 and lower surface 24 is now applied between the upper surface and the skin. Sensing circuit 50 detects application of the pad with the skin due to reduced resistance between conductor 36 and electrode 37, which is now in contact with the skin.

When microcontroller 48 receives a signal from sensing circuit 50 indicative of the skin contact, or when actuated by the user, it instructs polarity switch 46 to reverse the polarity of the voltage applied between coating 32 and the skin for a short time, preferably about 0.1 sec. In consequence, powder 28 is repelled from upper surface 22 and instead adheres to the skin. Preferably, the microcontroller delays reversing the potential for at least several seconds, to ensure that the pad has been firmly applied before the powder is released. After releasing the powder, the microcontroller shuts off converter 44, so that the voltage applied by the device is reduced to zero. The pad is left in place to cover the powder while it is gradually absorbed into the body.

Various means may be used to cause powder 28 to penetrate through the skin, so that it is absorbed in sub-dermal tissue layers. Ordinarily, skin moisture under surface 22 will dissolve or otherwise mobilize the dry powder, so that it is gradually carried into the skin. Alternatively or additionally, the skin may be prepared to receive the powder by ablation of the outer skin layer, known as the stratum corneum, using any suitable method known in the art, for example, laser or thermal ablation.

FIGS. 6A, 6B and 6C are schematic, sectional illustrations showing a device 50 for ablation of the outer skin layer and transdermal delivery of powder 28 therethrough, in accordance with a preferred embodiment of the present invention. Device 50 combines electrical ablation of the stratum corneum with the electrostatic principles of device 20, as described hereinabove. For this purpose, an array of micro-electrodes 52 is formed on the inside of upper surface 22, and the micro-electrodes are driven, preferably by an AC driver circuit 54, to create micro-channels in the stratum corneum, as described in the above-mentioned U.S. patent application. Preferably, the dimensions of the micro-electrodes and the spacing therebetween are on the order of 0.1 to 0.3 mm. Further preferably, driver circuit 54 drives the micro-electrodes at a frequency of about 10 kHz, although other frequencies between about 100 Hz and 10 MHz may also be used.

Before application of device 50 to the skin, electrodes 52 are inactive, and switching circuit 42 is actuated to applying a positive voltage to coating 32. Thus, powder 28 adheres to the inside of surface 22, generally in between the electrodes, as shown in FIG. 6A. Lower surface 24 is peeled away, and the upper surface with the powder is placed against skin 60 of the subject, as shown in FIG. 6B. These steps are substantially the same as those described hereinabove with reference to device 20 and the method of FIG. 5.

With surface 22 in place against skin 60, driver 54 is operated to generate high-frequency AC currents between mutually neighboring electrodes 52. The currents pass through the stratum corneum, as indicated by arrows 62 in FIG. 6B. Preferably, the driving frequency of the AC currents is between about 10 kHz and 1 MHz, which has been found to be effective in ablating the stratum corneum, but is too high a frequency to have a substantial effect on the particles of powder 28.

The effect of the current between electrodes 52 is to create micro-channels 64, i.e., small passageways through the stratum corneum in between the electrodes, as shown in FIG. 6C. Once the micro-channels have been created, driver 54 shuts off the AC current flow through the electrodes, preferably as described in the above-referenced patent application. Switching circuit 42 then reverses the electrical polarity of coating 32 relative to skin 60, causing powder 28 to be driven off surface 22 and into micro-channels 64. Penetration of the powder through the skin is thus enhanced.

Although switching circuitry 42 is shown in the figures as being coupled to coating 32 via a single, common connection for the entire area of the coating, in other preferred embodiments of the present invention, coating 32 is divided into a plurality of separate regions, which may be individually addressed by circuitry 42. For example, each region between a pair of electrodes 52 in device 50 may be individually addressed, or group of such regions may be addressed together. After the device is affixed to the skin, each of the regions is actuated by reversing the voltage polarity applied respectively thereto, according to a predetermined sequence. In this manner, the device may be used to divide the total dose of powder 28 inside the envelope into smaller sub-doses, which are administered in sequence over time according to a desired dosage rate.

It will be appreciated that the preferred embodiments described above are cited by way of example, and the full scope of the invention is limited only by the claims.

I claim:

1. A device for delivery of a powder to the skin of a subject, comprising:

a pad, comprising an insulating material and having an upper side and a lower side, which lower side is placed against the skin after application of the powder thereto; and an electrical power source, which applies an electrical potential to the pad, causing the powder to adhere by electrostatic force to the lower side of the pad, and which alters the potential so that the powder is released from the pad and the powder contacts the skin against which the pad is placed.

2. A device according to claim 1, wherein the pad comprises an electrically conductive coating on the upper side thereof, to which the power source applies the potential.

3. A device according to claim 2, wherein the conductive coating is segmented, such that the power source reverses the polarity of the potential substantially independently in two or more segments of the coating.

4. A device according to claim 1, and comprising an envelope in which the powder is contained before delivery of the powder to the skin, the envelope comprising an upper and a lower surface, wherein the upper surface comprises the pad, and the lower surface is separated from the pad before the lower side of the pad is placed against the skin.

5. A device according to claim 4, wherein the envelope comprises an electrically conductive region therein, which contacts the powder in the envelope and imparts electrical charge thereto.

6. A device according to claim 5, wherein the power source applies the electrical potential between the upper and lower surfaces of the envelope, and wherein the electrically conductive region comprises a conductive coating on the lower surface.

7. A device according to claim 6, and comprising a conductor coupled to the power source, which contacts the skin after the lower surface is separated from the pad so that the power source applies the electrical potential between the pad and the skin.

8. A device according to claim 1, wherein the power source comprises a battery and a switching circuit coupled thereto.

9. A device according to claim 8, wherein the switching circuit comprises a voltage converter, which steps up a voltage supplied by the battery so that the electrical potential applied to the pad is substantially greater than the battery voltage.

10. A device according to claim 8, wherein the switching circuit comprises a polarity switch, which applies the electrical potential to the pad, causing the powder to adhere thereto, at a first polarity, and which reverses the polarity so as to cause the powder to be released.

11. A device according to claim 8, and comprising a sensor, which generates a signal responsive to an operational state of the device, wherein the switching circuit receives the signal from the sensor and controls operation of the device responsive thereto.

12. A device according to claim 11, wherein the sensor comprises at least one electrode, which senses an electrical resistance that varies responsive to the operational state.

13. A device according to claim 11, wherein the power source is fixed to the pad before operation thereof, and wherein the sensor generates the signal responsive to fixing of the power source to the pad.

14. A device according to claim 11, and comprising an envelope in which the powder is contained before delivery of the powder to the skin, and wherein the sensor generates the signal responsive to opening of the envelope in preparation for placing the pad against the skin.

15. A device according to claim 11, wherein the sensor generates the signal responsive to placement of the pad against the skin.

16. A device according to claim 1, and comprising means for ablating an outer layer of the skin through which the powder is delivered.

17. A device according to claim 16, wherein the means for ablating comprises an array of electrodes between which an electrical current is driven so as to create channels through the outer skin layer.

18. A device according to claim 17, wherein the electrodes in the array are mutually spaced by less than about 0.3 mm.

19. A device according to claim 17, wherein the electrical current is driven between the electrodes at a frequency greater than about 100 Hz.

20. A method for delivery of a powder to the skin of a subject, comprising:

bringing a quantity of the powder into proximity with a pad having upper and lower sides;

applying an electrical potential to the pad, so that the powder adheres to the lower side of the pad by electrostatic force;

placing the lower side of the pad with the powder against the skin; and altering the electrical potential, so that the powder is released from the pad and contacts the skin against which the pad is placed.

21. A method according to claim 20, wherein bringing the quantity of the powder into proximity with the pad comprises filling an envelope with the powder, the envelope comprising an upper and a lower surface, the upper surface comprising the pad, and wherein placing the lower side of the pad against the skin comprises separating the lower surface from the pad before the lower side of the pad is placed against the skin.

22. A method according to claim 21, wherein applying the electrical potential comprises applying a potential to an electrically conductive region in the envelope, which contacts the powder in the envelope and imparts electrical charge thereto.

23. A method according to claim 21, wherein applying the electrical potential comprises applying a potential between the upper and lower surfaces of the envelope.

24. A method according to claim 23, wherein applying the electrical potential comprises applying potential of a first polarity, and wherein altering the electrical potential comprises reversing the polarity.

25. A method according to claim 24, wherein the electrical potential of reversed polarity is applied between the pad and the skin.

26. A method according to claim 20, and comprising ablating an outer layer of the skin through which the powder is delivered.

27. A method according to claim 26, wherein ablating the outer layer comprises applying an electrical current through the skin so as to create channels through the outer skin layer.

28. A method according to claim 27, wherein applying the electrical current comprises applying an alternating current.

29. A method according to claim 20, wherein altering the potential comprises altering the potential in a graduated manner so that the powder is delivered over time in a sequence of sub-doses.

30. A method according to claim 29, wherein the pad comprises multiple regions, and wherein altering the potential comprises altering the potential at different times in two or more of the regions, so that the powder is delivered from the different regions of the pad at the different, respective times.

31. A method according to claim 20, and comprising sensing an operational state of the pad, and controlling the delivery of the powder responsive to the state.

32. A method according to claim 31, wherein sensing the operational state comprises detecting placement of the lower side of the pad against the skin, and wherein controlling the delivery comprises providing a control signal to alter the electrical potential after the placement is detected.

33. A method according to claim 31, wherein sensing the operational state comprises sensing an electrical resistance indicative of the state.

* * * * *